United States Patent
Kelly (10) Patent No.: US 10,034,741 B2
(45) Date of Patent: Jul. 31, 2018

(54) PARARENAL STENT GRAFT AND METHODS FOR USE

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 220 days.

(21) Appl. No.: 14/636,249

(22) Filed: Mar. 3, 2015

(65) Prior Publication Data

US 2015/0209135 A1    Jul. 30, 2015

Related U.S. Application Data

(63) Continuation of application No. 14/311,733, filed on Jun. 23, 2014, now Pat. No. 8,998,971.

(Continued)

(51) Int. Cl.
*A61F 2/06* (2013.01)
*A61F 2/07* (2013.01)
(Continued)

(52) U.S. Cl.
CPC .............. *A61F 2/07* (2013.01); *A61F 2/064* (2013.01); *A61F 2/852* (2013.01); *A61F 2/88* (2013.01); *A61F 2002/061* (2013.01); *A61F 2002/8486* (2013.01); *A61F 2220/0008* (2013.01); *A61F 2220/0033* (2013.01);
(Continued)

(58) Field of Classification Search
CPC ...... A61B 17/12022; A61F 2/82; A61F 2/954; A61F 2002/823
See application file for complete search history.

(56) References Cited

U.S. PATENT DOCUMENTS 6,306,164 B1   10/2001   Kujawski
6,325,819 B1   12/2001   Pavcnik et al.
(Continued)

FOREIGN PATENT DOCUMENTS

WO   2014/172501   10/2014
WO   2015/116715    8/2015

OTHER PUBLICATIONS

International Search Report for Application PCT/US2014/043651, dated Oct. 8, 2014.
(Continued)

*Primary Examiner* — Julie A Szpira
(74) *Attorney, Agent, or Firm* — McDonnel Boehnen Hulbert & Berghoff LLP (57) ABSTRACT

Example stent grafts and methods for placement thereof are provided. An example stent graft may include (a) a main body stent graft defining a lumen having an inlet defined at a proximal end of the main body stent graft and having an outlet defined at a distal end of the main body stent graft, (b) a visceral-vessel opening defined in a sidewall of the main body stent graft between the proximal end and the distal end of the main body stent graft, (c) a diaphragm disposed within the lumen of the main body stent graft and coupled to the main body stent graft, wherein a first renal inlet, a second renal inlet, an infrarenal inlet and a visceral inlet are defined in the diaphragm and (d) a visceral chamber defined by a sidewall coupled to the visceral inlet and to the visceral-vessel opening.

28 Claims, 6 Drawing Sheets

Related U.S. Application Data (60) Provisional application No. 61/932,280, filed on Jan. 28, 2014.

(51) Int. Cl.
    *A61F 2/852*     (2013.01)
    *A61F 2/88*     (2006.01)
    *A61F 2/848*     (2013.01)

(52) U.S. Cl.
    CPC ................ *A61F 2230/0091* (2013.01); *A61F 2250/0039* (2013.01); *A61F 2250/0069* (2013.01)

(56) References Cited

U.S. PATENT DOCUMENTS

| | | | |
|---|---|---|---|
| 6,395,018 B1 * | 5/2002 | Castaneda | A61F 2/07 623/1.13 |
| 6,585,756 B1 | 7/2003 | Strecker | |
| 6,635,080 B1 | 10/2003 | Lauterjung et al. | |
| 6,942,692 B2 | 9/2005 | Landau et al. | |
| 7,014,653 B2 | 3/2006 | Ouriel et al. | |
| 7,122,052 B2 | 10/2006 | Greenhalgh | |
| 8,105,372 B1 | 1/2012 | Chuter | |
| 8,221,494 B2 * | 7/2012 | Schreck | A61F 2/07 623/1.1 |
| 8,845,714 B2 * | 9/2014 | DiMatteo | A61F 2/07 623/1.13 |
| 2002/0058986 A1 | 5/2002 | Landau et al. | |
| 2002/0058993 A1 * | 5/2002 | Landau | A61F 2/064 623/1.35 |
| 2002/0169497 A1 | 11/2002 | Wholey et al. | |
| 2003/0120330 A1 | 6/2003 | Ouriel et al. | |
| 2003/0130720 A1 | 7/2003 | DePalma et al. | |
| 2004/0073288 A1 | 4/2004 | Kerr | |
| 2004/0193245 A1 | 9/2004 | Deem et al. | |
| 2006/0184228 A1 | 8/2006 | Khoury | |
| 2008/0262595 A1 | 10/2008 | Chu et al. | |
| 2009/0024072 A1 | 1/2009 | Criado et al. | |
| 2009/0240316 A1 | 9/2009 | Bruszewski et al. | |
| 2009/0287145 A1 | 11/2009 | Cragg et al. | |
| 2011/0166644 A1 | 7/2011 | Keeble et al. | |
| 2012/0191174 A1 * | 7/2012 | Vinluan | A61F 2/07 623/1.12 |
| 2012/0197382 A1 | 8/2012 | Roeder et al. | |
| 2013/0144373 A1 | 6/2013 | Shahriari et al. | |
| 2013/0172984 A1 | 7/2013 | Greenberg et al. | |
| 2014/0316513 A1 | 10/2014 | Tang et al. | |
| 2015/0105850 A1 | 4/2015 | Shahriari | |

OTHER PUBLICATIONS

International Search Report PCT/US2016/024125, dated Jun. 17, 2016.

International Search Report for Application PCT/US2015/013344, dated May 6, 2015.

\* cited by examiner

PARARENAL STENT GRAFT AND METHODS FOR USE

CROSS-REFERENCE TO RELATED APPLICATION

This application is a continuation of U.S. patent application Ser. No. 14/311,733, filed Jun. 23, 2014, which claims the benefit of the filing date of U.S. Provisional Patent Application Ser. No. 61/932,280, filed Jan. 28, 2014, which are hereby incorporated by reference in their entireties.

BACKGROUND

Unless otherwise indicated herein, the materials described in this section are not prior art to the claims in this application and are not admitted to be prior art by inclusion in this section.

Pararenal and juxtarenal aneurysms are infrarenal aneurysms located within about 5 mm of the renal arteries that have very short necks (i.e., less than 5 mm) or that involve 2-3 visceral arteries (e.g., right and left renal arteries and occasionally the superior mesenteric artery ("SMA")) and that extend to within about 5 mm of the SMA. Since a pararenal aneurysm typically includes only a portion of the visceral trunk of the aorta, obtaining a proximal seal between a main body stent graft and the vascular tissue is difficult since blood flow must be maintained to the renal arteries, the SMA and the celiac artery. One technique to treat a pararenal aneurysm may involve placing bridging stent grafts in each of the foregoing arteries via a branched or manifold stent graft, for example. While this technique may provide a sufficient proximal seal between the stent graft and the vasculature, the proximal seal may also create a new risk, namely that blood flow to the lumbar arteries may be blocked by the proximal seal. Specifically, the lumbar arteries perfuse the spinal cord with blood, and they tend to be concentrated in the area of the thoracic aorta above the celiac arteries in the "seal zone" for stent grafts placed and anchored in the aorta. As such, cutting off blood flow to the lumbar arteries may cause a patient to become hemodynamically unstable (i.e., blood pressure is too low to sufficiently perfuse tissues with blood) and may put a patient at risk for paraplegia.

SUMMARY

Example embodiments beneficially provide stent grafts for treating pararenal aneurysms, for example, and methods for placing these stent grafts. The pararenal stent graft disclosed herein provides several advantages over known techniques. For example, the pararenal stent graft may permit a pararenal aneurysm to be repaired endovascularly with minimal coverage of the aorta above the celiac artery. This may be accomplished through an indentation or scallop-shaped-hole defined at the proximal end of the main body stent graft and arranged below the lumbar arteries upon deployment in vivo, while the remainder of the proximal end of the stent graft extends along the visceral trunk of the aorta. The proximal end of the main body stent graft may in turn be supported by a proximal sealing ring having a bi-level construction defining an upper portion arranged along the most proximal edge of the main body stent graft and a lower portion arranged along the indentation or scallop-shaped hole.

In addition, the pararenal stent graft may beneficially provide a diaphragm disposed within the main lumen that defines a first renal inlet, a second renal inlet, an infrarenal inlet and a visceral inlet. This arrangement may permit one or more bridging stents that may be coupled directly to these inlets or to stent grafts coupled to these inlets. This allows the exclusion of an aneurysm distal to the main body stent graft down through the iliac arteries, for example.

Further, in one embodiment, first and second renal artery stent grafts may be coupled to the renal inlets of the diaphragm and may be arranged to cross-over one another with gentle swooping paths for stenting to the renal arteries. This configuration may advantageously permit unobstructed blood flow and may minimize both the potential for kinking of the stent grafts and for turbulent blood flow. Also, in a further embodiment, the first and second renal inlets may be positioned on opposite sides of the diaphragm between the sidewall of the main body stent graft and the center of the lumen defined by the main body stent graft. This arrangement may provide for a gentle swooping path of the first and second renal lumens, because free ends of the lumens may have more space to cross to the opposite side of the main body stent graft. In an alternative embodiment, the first and second renal inlets may be positioned in the diaphragm closer to the center of the lumen defined by the main body stent graft. This arrangement may beneficially result in a higher blood flow rate.

Also, in one embodiment, a visceral chamber may be defined by a sidewall coupled to both the visceral inlet of the diaphragm and to a visceral-vessel opening defined in a sidewall of the main body stent graft. This visceral chamber may beneficially permit native blood flow to continue to the celiac and SMA arteries. In addition, in the event that an aneurysm advances proximally after placement of the pararenal stent graft, the aneurysm may be repaired by a standard thoracic stent graft that may be deployed and mate directly with the lumen of the main body stent graft.

Thus, in one aspect, a stent graft is provided including the features of (a) a main body stent graft defining a lumen having an inlet defined at a proximal end of the main body stent graft and having an outlet defined at a distal end of the main body stent graft, (b) a visceral-vessel opening defined in a sidewall of the main body stent graft between the proximal end and the distal end of the main body stent graft, (c) a diaphragm disposed within the lumen of the main body stent graft and coupled to the main body stent graft, wherein a first renal inlet, a second renal inlet, an infrarenal inlet and a visceral inlet are defined in the diaphragm and (d) a visceral chamber defined by a sidewall coupled to the visceral inlet and to the visceral-vessel opening.

In a second aspect, a method for placement of the stent graft is provided including the steps of (a) introducing a guidewire into any appropriately sized arterial configuration via arterial access, (b) loading a delivery catheter containing the stent graft according to the first aspect onto the guidewire, (c) moving the delivery catheter along the guidewire and introducing the delivery catheter into the appropriately sized arterial configuration via arterial access, and (d) deploying the stent graft into the appropriately sized arterial configuration and/or a lumen of a previously-placed stent graft.

These as well as other aspects, advantages, and alternatives, will become apparent to those of ordinary skill in the art by reading the following detailed description, with reference where appropriate to the accompanying drawings.

DETAILED DESCRIPTION

Example stent grafts, as well as methods of placement of the stent grafts, are described herein. Any example embodiment or feature described herein is not necessarily to be construed as preferred or advantageous over other embodiments or features. The example embodiments described herein are not meant to be limiting. It will be readily understood that certain aspects of the disclosed methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, "about" means +/−5%.

As used herein, "pararenal" means a region adjacent to the kidney.

As used herein, "infrarenal" means situated or occurring below the kidneys.

As used herein, "visceral trunk" refers to the portion of the aorta attached to the renal arteries, superior mesenteric artery ("SMA"), and the celiac artery.

As used herein, "proximal end" refers to the end of the main body stent graft that will be positioned closer to a patient's heart than the "distal end" upon deployment.

As used herein, a "sealing ring" is a structure configured to apply an outward circumferential force to create a fluid tight seal. In some embodiments, this circumferential force may be applied laterally against the sidewall of the main body stent graft. In other embodiments, the circumferential force may be applied to maintain a hole or opening in a sidewall of the main body stent graft both in an open condition and in contact with vasculature. A sealing ring may be circular or oval, may be continuous or discontinuous, and/or may be contoured or have a bi-level shape to accommodate indentations or scallop-shaped holes in the sidewall of the main body stent graft, among other possibilities. The sealing rings may include elastic recoil material, such as nitinol, a standard sinusoidal stent structure or a straight reinforced wire, among other possibilities.

As used herein, "passive fixation" refers to friction, interaction between the cloth of the grafts, radial strength of the stent and blood pressure that holds the component stent grafts together at the site of overlap.

As used herein, "active fixation" refers to features coupled to a stent, graft, or stent graft that may actively engage vasculature or another stent graft, including hooks, bi-directional hooks, anchors, staples, bio-activated adhesive, or a combination thereof, among other possibilities.

As used herein, with respect to measurements, "about" means +/−5%.

As used herein, a "stent graft" is a tubular, radially-expandable device comprising a fluid-tight fabric supported by a stent and may be used to bridge diseased arteries. Such stent grafts and methods for their deployment and use are known to those of skill in the art. For example, vascular sheaths can be introduced into the patient's arteries, through which items, including but not limited to, guidewires, catheters and, eventually, the stent graft, are passed.

As used herein, "stent" is typically a cylindrical frame and means any device or structure that adds rigidity, expansion force, or support to a prosthesis or native vasculature, while "stent graft" refers to a prosthesis comprising a stent and a graft material associated therewith that forms a fluid-tight lumen through at least a portion of its length. For example, the stent structure may comprise coiled, mesh, zig-zag or woven wires or a laser cut tube. A "graft" is a substantially cylindrical liner that may be disposed on the stent's interior, exterior or both. In some embodiments, grafts may be woven as unitary structures with multiple lumens. For example, the main body stent graft, the diaphragm, the two renal lumens, the infrarenal lumen and the visceral chamber may all be woven together as a unitary structure or otherwise joined together to form a unitary structure. Further, when used in combination with a graft, the stent structure may further comprise a series of spaced apart stent rings disposed along the graft. A wide variety of attachment mechanisms are available to join the stent and graft together, including but not limited to, sutures, adhesive bonding, heat welding, and ultrasonic welding.

The stent can be made of any suitable material, including but not limited to biocompatible metals, implantable quality stainless steel wires, nickel and titanium alloys, and biocompatible plastics attached to a graft. Any suitable fluid tight graft material can be used. In a preferred embodiment, the graft material is a biocompatible fabric, including but not limited to woven or knitted polyester, such as poly(ethylene terephthalate), polylactide, polyglycolide and copolymers thereof; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages, woven nickel-titanium and polyurethanes containing siloxane segments. Materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. The graft material may also include extracellular matrix materials.

The covered stent grafts can be made of any suitable material, including but not limited topolytetrafluoroethylene (ePTFE) lined nickel-titanium alloy stent. The stent grafts are preferably covered and flexible. The stent grafts may contain any other suitable components, such as surface modifications including but not limited to covalent attachment of heparin.

In one aspect, the invention provides a stent graft, comprising:

a main body stent graft defining a lumen having an inlet defined at a proximal end of the main body stent graft and having an outlet defined at a distal end of the main body stent graft;

a visceral-vessel opening defined in a sidewall of the main body stent graft between the proximal end and the distal end of the main body stent graft;

a diaphragm disposed within the lumen of the main body stent graft and coupled to the main body stent graft, wherein a first renal inlet, a second renal inlet, an infrarenal inlet and a visceral inlet are defined in the diaphragm; and a visceral chamber defined by a sidewall coupled to the visceral inlet and to the visceral-vessel opening.

Referring now to FIGS. 1-6, a stent graft 100 is shown including a main body stent graft 105 defining a lumen having an inlet 106 defined at a proximal end 107 of the main body stent graft 105 and having an outlet 108 defined at a distal end 109 of the main body stent graft 105. In one embodiment, a portion of the lumen of the main body stent graft 105 arranged between the diaphragm 110 and the proximal end 107 of the main body stent graft 105 may have a diameter ranging from about 20 mm to about 46 mm. In another embodiment, the main body stent graft 105 may have a length ranging from about 20 mm to about 80 mm extending between the proximal end 107 of the main body stent graft 105 and the proximal end 116 of the visceral-vessel opening 115. In a further embodiment, the main body stent graft 105 may have a length ranging from 0 mm to about 40 mm extending between the distal end 117 of the visceral-vessel opening 115 and the distal end 109 of the main body stent graft 105.

Figure 1:
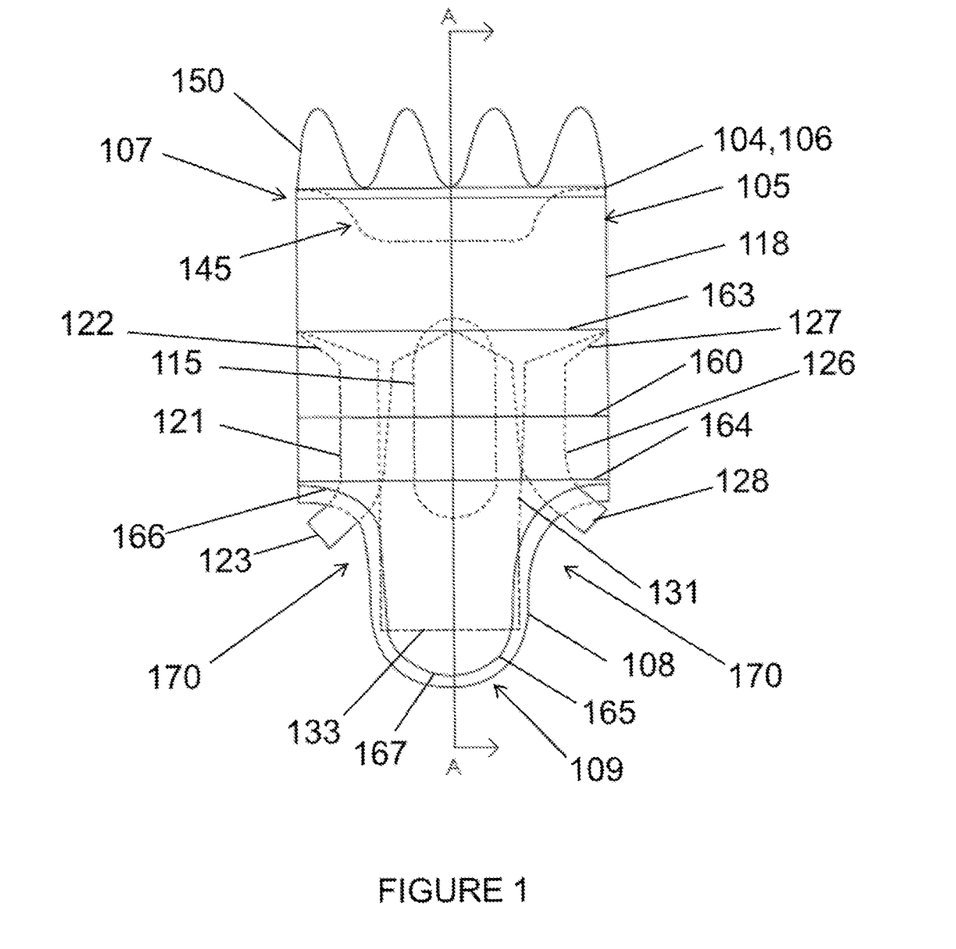
FIG. 1 is a front view of the stent graft according to one example embodiment.
Figure 2:
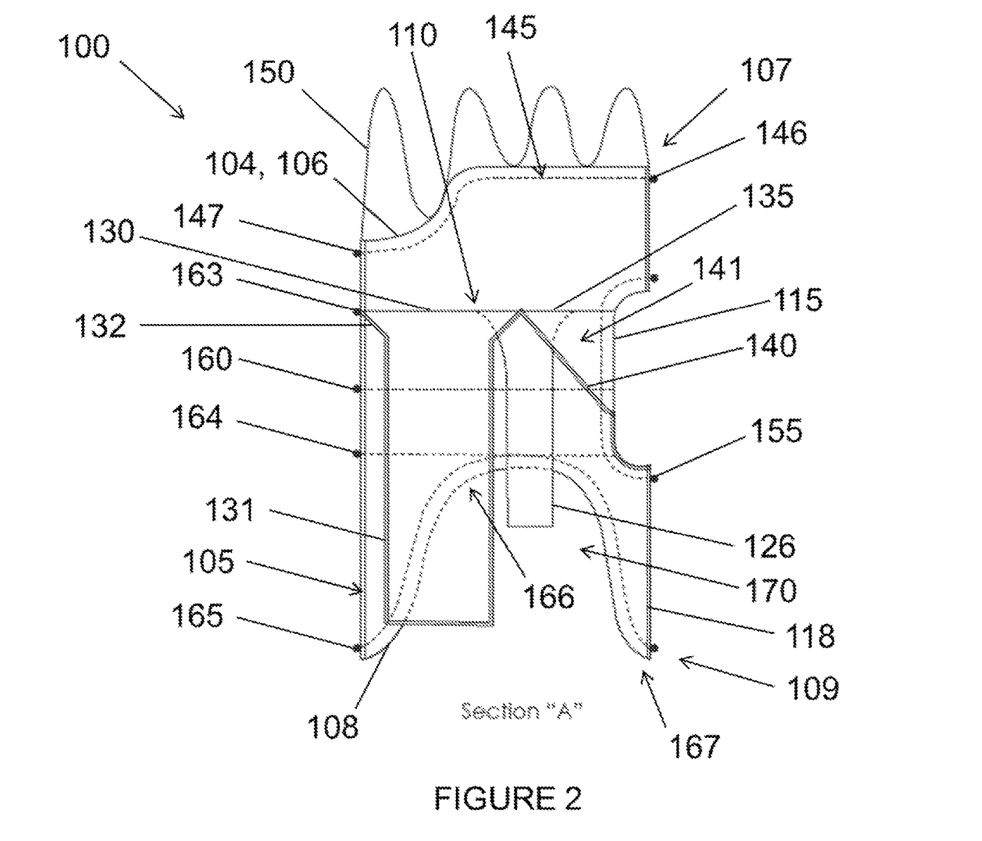
FIG. 2 is a cross-sectional side view of Section A:A from FIG. 1.
Figure 3:
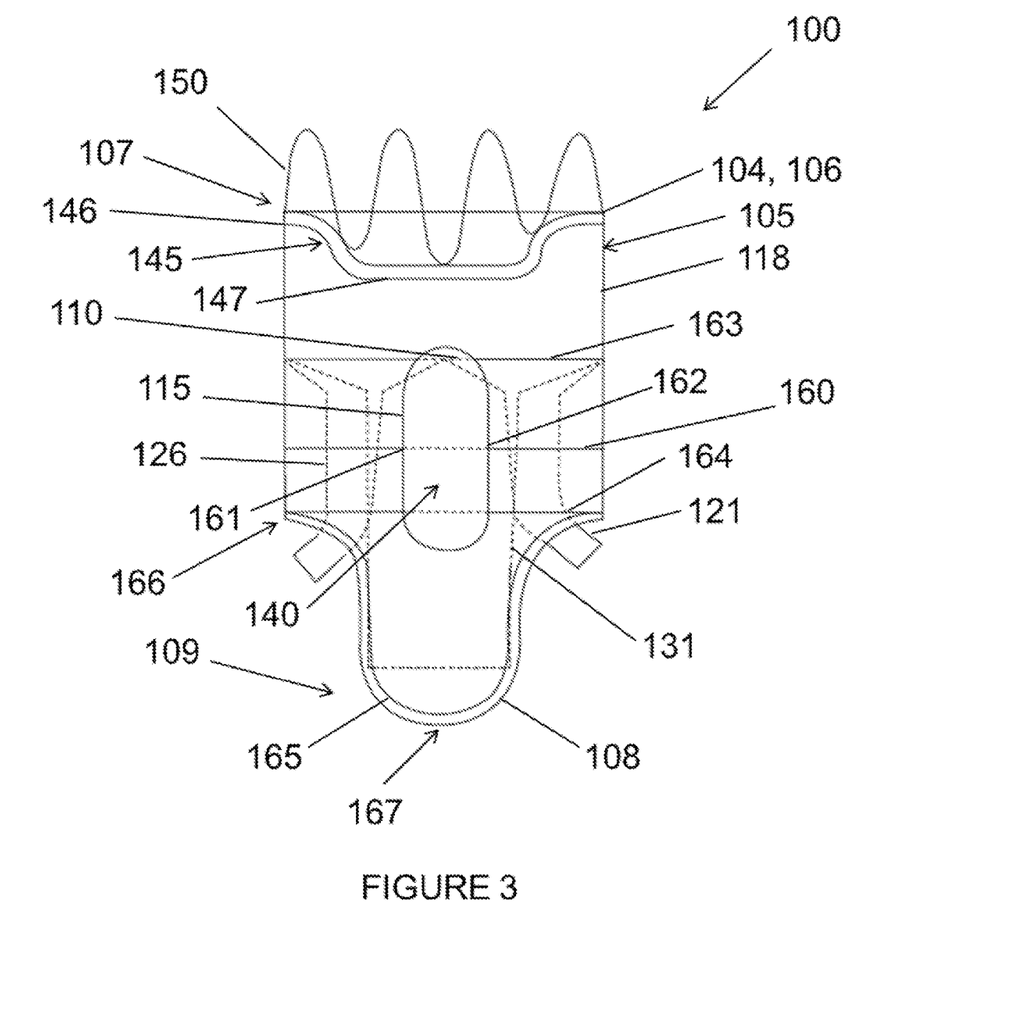
FIG. 3 is a back view of the stent graft according to the example embodiment of FIG. 1.
Figure 4:
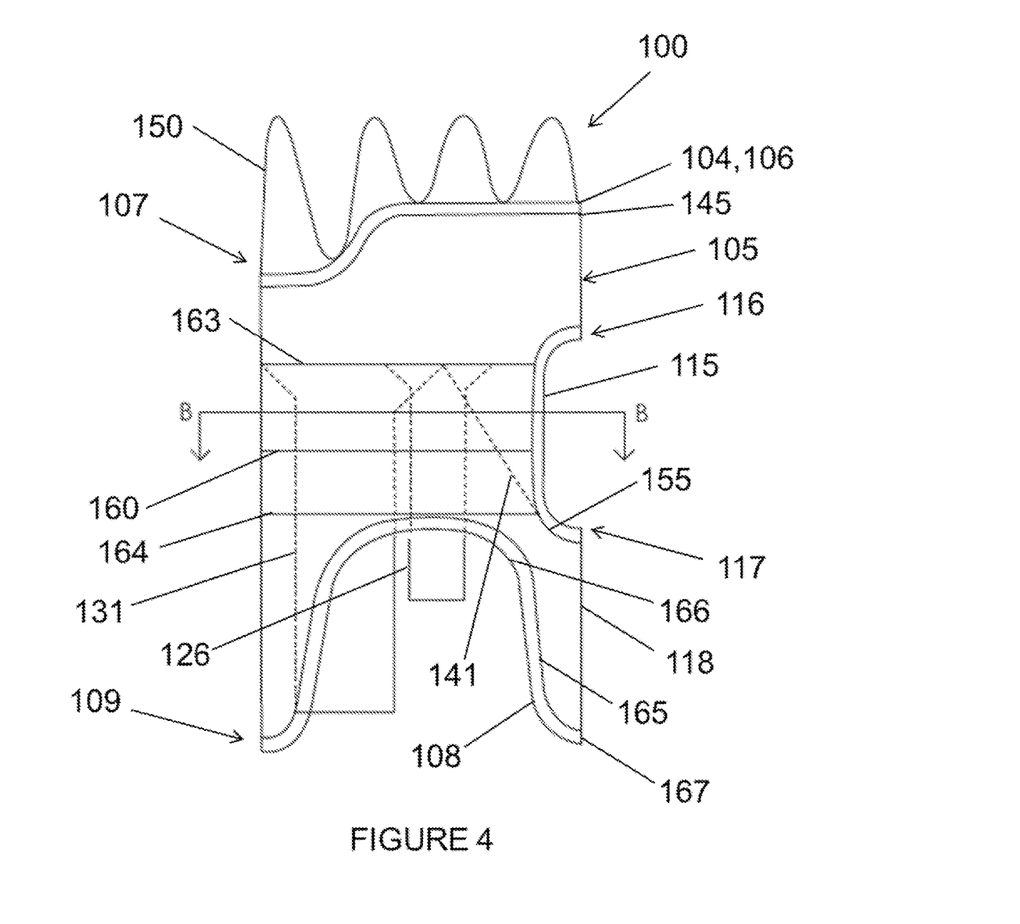
FIG. 4 is a side view of the stent graft according to the example embodiment of FIG. 1.
Figure 5:
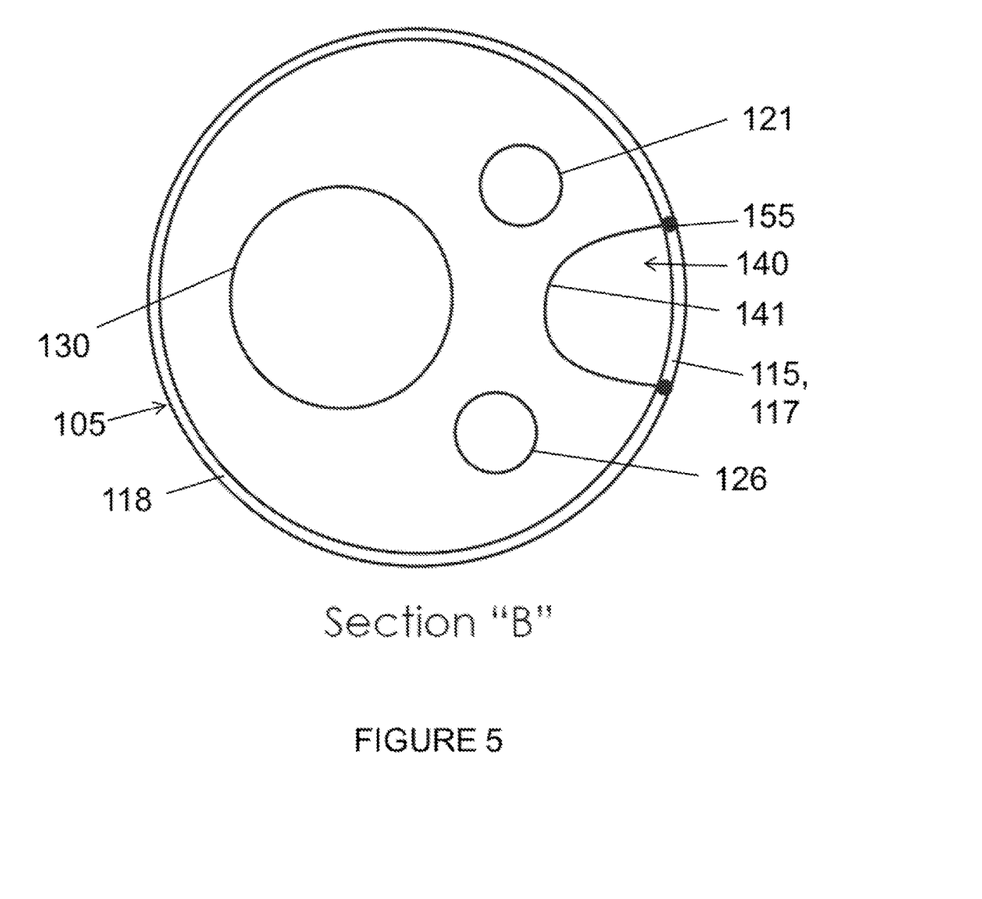
FIG. 5 is a cross-sectional top view of Section B:B from FIG. 4.
Figure 6:
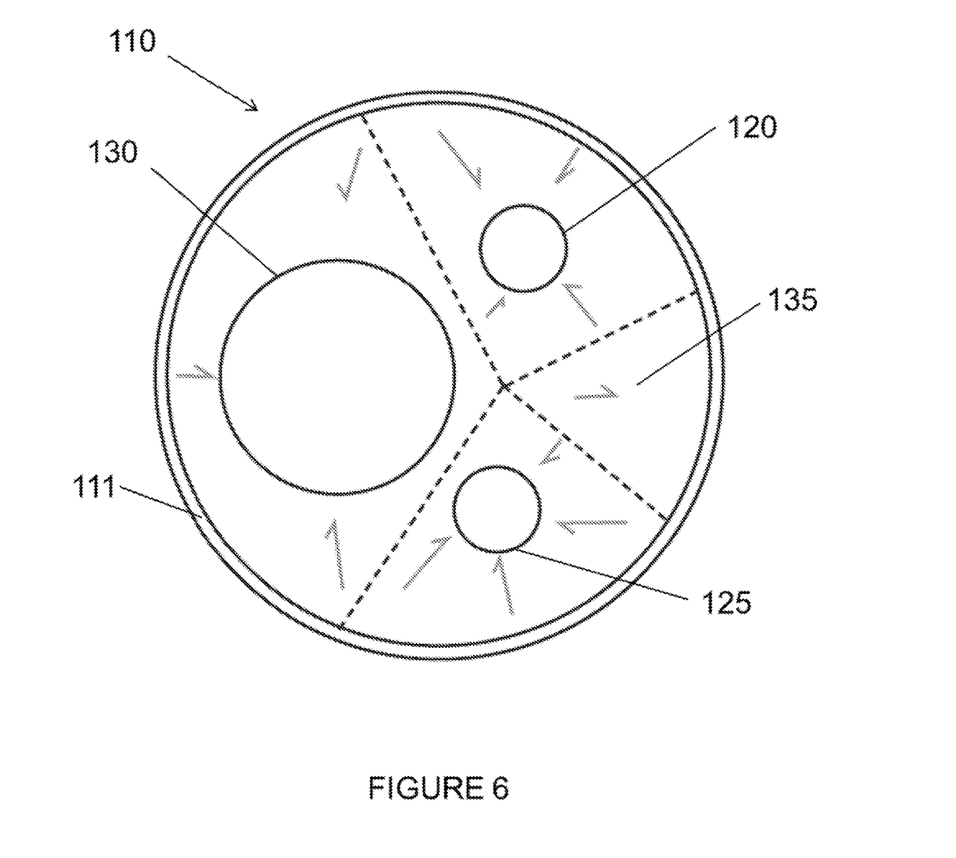
FIG. 6 is a top view of the stent graft according to the example embodiment of FIG. 1.

The stent graft 100 includes a diaphragm 110 disposed within the lumen of the main body stent graft 105 and coupled to the main body stent graft 105. The diaphragm 110 defines a first renal inlet 120, a second renal inlet 125, an infrarenal inlet 130 and a visceral inlet 135. The visceral inlet may be aligned in a quadrant of the diaphragm that lies above the visceral-vessel opening 115, discussed in more detail below, and the infrarenal inlet 130 and the first and second renal inlets 120, 125 may be arranged in various configurations in the same or other quadrants of the diaphragm 110. For example, in one embodiment, as shown in FIG. 6, the infrarenal inlet 130 and the visceral inlet 135 may be arranged on opposite sides of the diaphragm 110 with the first renal inlet 120 and the second renal inlet 125 likewise arranged on opposite sides of the diaphragm 110 between the infrarenal inlet 130 and the visceral inlet 135. Alternatively, the first and second renal inlets 120, 125 may be arranged on the same side of the diaphragm 110 between the infrarenal inlet 130 and the visceral inlet 135. In other embodiments, the infrarenal inlet 130 and one of the first and second renal inlets 120, 125 and may be arranged on opposite sides of the diaphragm 110 with the other renal inlet arranged therebetween. In a further embodiment, the infrarenal inlet 130 and the renal inlets 120, 125 may be arranged such that there is no other inlet directly opposite the visceral inlet 135.

In one embodiment, the diaphragm 110 may be sloped or tapered in the regions surrounding these various inlets. In one embodiment, the visceral inlet 135 may be defined as a V-shape, a half-circle having a radius ranging from about 5 mm to about 15 mm or a complete circular opening with a diameter ranging from about 8 mm to about 12 mm, among other possibilities. In further embodiments, the first renal inlet 120, second renal inlet 125, infrarenal inlet 130 may have a substantially circular shape. In one embodiment, a first renal stent graft 121, a second renal stent graft 126 and an infrarenal stent graft 131 may be directly coupled to the first renal inlet 120, the second renal inlet 125 and the infrarenal inlet 130, respectively, in fluid-tight manner prior to deployment of the stent graft 100. The first and second renal stent grafts 121, 126 and the infrarenal stent graft 131 each define a lumen and are configured to receive extension or bridging stent grafts that may be held in place via passive or active fixation. This arrangement may provide blood flow between the stent graft 100 and the renal arteries and or may provide blood flow to the infrarenal arteries including, for example, the aorta and the common iliac arteries.

In various embodiments, the infrarenal lumen 131 and the renal lumens 121, 126 may be straight or gradually sweeping and their distal free ends 123, 128, 133 may be freely moved to place bridging stent grafts. In one embodiment, the infrarenal lumen 131 may have a length of at least 30 mm. In another embodiment, the length of the infrarenal lumen may range from about 10 mm to 60 mm. An another embodiment, the infrarenal lumen 131 may have may have a diameter ranging from about 10 mm to about 25 mm. In another embodiment, the infrarenal inlet 130 may have a diameter ranging from about 10 mm to about 25 mm. In yet another embodiment, the diameter of the infrarenal inlet 130 may be larger than the diameter of the infrarenal lumen 131 such that a proximal end of the infrarenal lumen 131 is tapered 132. In other embodiments, the first and second renal inlets 120, 125 may each have a diameter ranging from about 4 mm to about 25 mm. In one embodiment, the first and second renal lumens 121, 126 may each have a diameter ranging from about 4 mm to about 12 mm. In a further embodiment, the diameter of each of the first and second renal inlets 120, 125 may be larger than the diameter of each of the first and second renal lumens 121, 126 such that a proximal end of each of the first and second renal lumens is tapered 122, 127. Tapering from the diaphragm inlets to the various lumens may aid with guidewire alignment and entry into the respective lumens to place extension or bridging stents and may encourage laminar blood flow. In another embodiment, the first renal stent graft 121, the second renal stent graft 126 and the infrarenal stent graft 131 may be placed separately after deployment. In this embodiment, the renal and infrarenal stent grafts 121, 126, 131 may have flared proximal ends that are arranged proximal of the diaphragm upon deployment.

In one embodiment, a pair of opposing helical stent structures may be coupled to and extend along the length of one or more of the first renal lumen 121, the second renal lumen 126 and the infrarenal lumen 131. The helical stent structures may prevent elongation of the lumens. These helical stent structures may be made from biocompatible materials with elastic shape memory, such as nitinol, stainless steel, plastics, polymers or any combination of such materials, among other possibilities.

In a further embodiment, the diaphragm 110 may have an expandable frame 111. This expandable frame 111 is configured to apply an outward radial force to the main body stent graft 105 in response to a downward force applied to the diaphragm 110. The downward force may be due to blood flow, for example. In one embodiment, the diaphragm 110 may be positioned within the lumen of the main body stent graft 105 at or between a proximal end 116 of the visceral-vessel opening 115 and a distal end 117 of the visceral-vessel opening 115.

The stent graft 100 also includes a visceral-vessel opening 115 defined in a sidewall 118 of the main body stent graft 105 between the proximal end 107 and the distal end 109 of the main body stent graft 105. In one embodiment, the visceral-vessel opening 115 may have a height ranging from about 10 mm to about 60 mm and may have a width ranging from about 5 mm to about 20 mm. In one embodiment, the visceral-vessel opening may be wider at a proximal end than at a distal end, which may provide more graft surface area between the visceral-vessel opening 115 and two renal openings 170 to provide a more robust seal between the stent graft and vasculature. In another embodiment, the visceral-vessel opening 115 may be covered with a flow-diverting material, for example, a high pick density braided or woven self-expanding stent material. This flow-diverting material may allow patency to the visceral vessels, for example, while minimizing the degree of unstented aortic wall to aid in anchoring the pararenal stent graft within vasculature. This may provide a more robust seal between the stent graft and aorta. The flow-diverting material may also permit formation of thrombus and arterial development therethrough, which may aid in appropriate blood flow and blood pressure through this region of the main body stent graft 105.

In addition, the stent graft 100 includes a visceral chamber 140 defined by a sidewall 141 coupled to the visceral inlet and to the visceral-vessel opening. The visceral chamber 140 may provide blood flow to the SMA and celiac arteries. In addition, a surgeon may utilize the visceral chamber 140 to place bridging stents in the SMA and/or celiac arteries In one embodiment, the stent graft 100 may further include a plurality of sealing rings coupled to the main body stent graft 105. In another embodiment, the plurality of sealing rings may include a proximal sealing ring 145 coupled to the main body stent graft 105 at or directly adjacent to the proximal end 107 of the main body stent graft 105. In a further embodiment, the proximal sealing ring 145 may have a bi-level construction defining an upper portion 146 and a lower portion 147. The lower portion 147 of the proximal sealing ring 145 may be aligned with and arranged proximal to the visceral-vessel opening 115, and the lower portion 147 may be arranged distal to the upper portion 146 of the proximal sealing ring 145. In one embodiment, the upper portion 146 of the proximal sealing ring 145 may be longitudinally spaced apart from the lower portion 147 along the main body stent graft 105 by a distance ranging from about 0 mm to about 40 mm. In the bi-level embodiment, a peripheral edge 104 of the proximal end 107 of the main body stent graft 105 may have the same bi-level contour as the proximal sealing ring 145. In one embodiment, the main body stent graft 105 may have a length ranging from about 0 mm to about 20 mm extending between the lower portion 147 of the proximal sealing ring 145 of the main body stent graft 105 and the proximal end 116 of the visceral-vessel opening 115.

The graft material of the main body stent graft 105 may have the same boundary as the proximal sealing ring 145 to avoid covering the lumbar arteries that deliver blood to the spine. In other embodiments, the graft material may have a uniform circumference along the upper boundary of the proximal sealing ring 145. In still further embodiments, the graft material may extend beyond the upper proximal boundary of the proximal sealing ring 145 to the top or proximal edge of a fixation stent 150.

In another embodiment, the plurality of sealing rings may include a visceral-vessel sealing ring 155 coupled to the main body stent graft 105 such that the visceral-vessel sealing ring 155 surrounds the visceral-vessel opening 115. For example, the visceral-vessel sealing ring 155 may apply a circumferential force to keep the visceral-vessel opening 115 intact upon deployment providing a fluid tight seal about the SMA and celiac arteries. The plurality of sealing rings may also include at least one support sealing ring 160 coupled to the main body stent graft 105 such that a first end 161 of the at least one support sealing ring 160 is coupled to a first side of the visceral-vessel sealing ring 155 and a second end 162 of the at least one support sealing ring 155 is coupled to a second side of the visceral-vessel sealing ring 155. The visceral-vessel sealing ring 155 may also work in combination with the support sealing ring 160 to provide a circumferential radial force relative to the main body stent graft 105 to provide a fluid tight seal with the aorta, for example. In a further embodiment, the at least one support sealing ring 160 may include a proximal support sealing ring 163, a distal support sealing ring 164 and a central support sealing ring 160. In one embodiment, the central support sealing ring 160 may be coupled to the visceral vessel sealing ring 155. The proximal support sealing ring 163 may be coupled to the main body stent graft 105 between the proximal end 107 of the main body stent graft 105 and the central support sealing ring 160. And the distal support sealing ring 164 may be coupled to the main body stent graft 105 between the distal end 109 of the main body stent graft 105 and the central support sealing ring 160.

In still another embodiment, the plurality of sealing rings may include a distal sealing ring 165 coupled to the main body stent graft 105 at or directly adjacent to the distal end 109 of the main body stent graft 105. In one embodiment, two renal openings 170 may be defined in the sidewall 118 of the main body stent graft 105 distal to the diaphragm 110. In one embodiment, the distal sealing ring 165 may have two radial portions 166 joined by two arch portions 167. The two arch portions 167 may be arranged longitudinally along the sidewall 118 of the main body stent graft 105 and the two radial portions 166 are arranged about the circumference of the main body stent graft 105. The two arch portions 167 are aligned with the two renal openings 170. In one embodiment, an effective diameter extending between the two radial portions 166 of the distal sealing ring 165 may range from about 20 mm to about 50 mm. In one embodiment, the two arch portions 167 may have a width ranging from about 4 mm to about 30 mm. In an embodiment in which renal openings 170 are not provided in the sidewall 118 of the main body stent graft 105, the length of the main body stent graft 105 may be shortened to permit the renal stent grafts to exit from the distal end 109 such that they are able to have a gentle sweep or large radius of curvature from the renal inlet and the target vessel ostium when bridging stents are placed.

In one embodiment, a bridging stent graft may comprise spaced-apart stent rings coupled to two wires longitudinally disposed along the length of and on opposite sides of the bridging stent graft. This arrangement may beneficially prevent elongation of the bridging stent graft. A 30 mm overlap with the renal stent grafts 121, 126 or infrarenal stent grafts 131 may be adequate to achieve passive fixation with a bridging stent graft during stent graft debranching procedures. The length of this overlap region may be less if active fixation features are also employed with the stent grafts, for example.

The stent grafts of the present invention may contain any further suitable components, including but not limited to radiopaque markers to aid in visualization and to facilitate accurate placement of the stent graft. These radiopaque markers may take the form of gold bands at the distal end of each individual lumen of a given stent graft or a directional marker, for example in the shape of an "S" or any other suitable form for indicating direction and orientation of the stent graft. In one embodiment, the proximal end 107 of the main body stent graft 105 may be coupled to a fixation stent 150. In addition, bi-directional anchoring hooks may be formed as part of the fixation stent 150 may be utilized to gain solid purchase in the non-diseased portion of a vessel wall. This fixation stent 150 may provide for radial-force fixation within the vessel in conjunction with bidirectional hooks. In another embodiment, the fixation stent 150 may be biased away from the lumen of the main body stent graft 105 to maintain fixation with vasculature in a deployed condition even if an aneurysm advances proximally.

In a second aspect, the invention provides a method for placement of the stent graft 100 according to the first aspect of the invention. The method includes (a) introducing a guidewire into any appropriately sized arterial configuration via arterial access, (b) loading a delivery catheter containing the stent graft of any of the foregoing embodiments onto the guidewire, (c) moving the delivery catheter along the guidewire and introducing the delivery catheter into the appropriately sized arterial configuration via arterial access and (d) deploying the stent graft into the appropriately sized arterial configuration and/or a lumen of a previously-placed stent graft.

In one embodiment, the second aspect may further include (e) loading a second delivery catheter containing a bridging stent graft onto the guidewire, (f) moving the second delivery catheter along the guidewire and introducing the second delivery catheter into the proximal end 107 of main body lumen of the stent graft 105 via arterial access, (g) selecting from among the first renal inlet 120, the second renal inlet 125, the infrarenal inlet 130 or the visceral inlet 135 defined in the diaphragm 110, (h) introducing the second delivery catheter into the selected inlet and into either a lumen 121, 126, 131 coupled to the selected inlet or an appropriately sized arterial lumen and (i) deploying all or a portion of the bridging stent graft into the selected inlet or the appropriately sized arterial lumen.

The above detailed description describes various features and functions of the disclosed stent grafts and methods for placement of the stent grafts with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A stent graft, comprising:
a main body stent graft defining a lumen having an inlet defined at a proximal end of the main body stent graft and having an outlet defined at a distal end of the main body stent graft;
a diaphragm disposed within the lumen of the main body stent graft and coupled to the main body stent graft, wherein a first renal inlet, a second renal inlet, an infrarenal inlet and a visceral inlet are defined in the diaphragm;
a first renal stent graft coupled to the first renal inlet, wherein the first renal stent graft defines a lumen;
a second renal stent graft coupled to the second renal inlet, wherein the second renal stent graft defines a lumen; and
an infrarenal stent graft coupled to the infrarenal inlet, wherein the infrarenal stent graft defines a lumen, wherein the diameter of the infrarenal inlet is larger than the diameter of the infrarenal lumen, wherein a proximal end of the infrarenal lumen is tapered and wherein a portion of the lumen of the main body stent graft arranged between the diaphragm and the proximal end of the main body stent graft has a diameter ranging from about 20 mm to about 46 mm.

2. The stent graft of claim 1, further comprising a visceral-vessel opening defined in a sidewall of the main body stent graft between the proximal end and the distal end of the main body stent graft.

3. The stent graft of claim 2, wherein the diaphragm is positioned within the lumen of the main body stent graft at or between a proximal end of the visceral-vessel opening and a distal end of the visceral-vessel opening.

4. The stent graft of claim 2, wherein the visceral-vessel opening has a height ranging from about 10 mm to about 60 mm and a width ranging from about 5 mm to about 20 mm.

5. The stent graft of claim 1, further comprising a visceral chamber defined by a sidewall coupled to the visceral inlet and to the visceral-vessel opening.

6. The stent graft of claim 1, further comprising a plurality of sealing rings coupled to the main body stent graft.

7. The stent graft of claim 6, wherein the plurality of sealing rings includes a proximal sealing ring coupled to the main body stent graft at or directly adjacent to the proximal end of the main body stent graft.

8. The stent graft of claim 7, wherein the proximal sealing ring has a bi-level construction defining an upper portion and a lower portion, wherein the lower portion of the proximal sealing ring is aligned with and arranged proximal to the visceral-vessel opening, wherein the lower portion of the proximal sealing ring is arranged distal to the upper portion of the proximal sealing ring and wherein a peripheral edge of the proximal end of the main body stent graft has the same contour as the proximal sealing ring.

9. The stent graft of claim 6, wherein the plurality of sealing rings includes a visceral-vessel sealing ring coupled to the main body stent graft such that the visceral-vessel sealing ring surrounds the visceral-vessel opening, and wherein the plurality of sealing rings includes at least one support sealing ring coupled to the main body stent graft such that a first end of the at least one support sealing ring is coupled to a first side of the visceral-vessel sealing ring and a second end of the at least one support sealing ring is coupled to a second side of the visceral-vessel sealing ring.

10. The stent graft of claim 9, wherein the at least one support sealing ring includes a proximal support sealing ring, a distal support sealing ring and a central support sealing ring, wherein the central support sealing ring is coupled to the visceral vessel sealing ring, wherein the proximal support sealing ring is coupled to the main body stent graft between the proximal end of the main body stent graft and the central support sealing ring, and wherein the distal support sealing ring is coupled to the main body stent graft between the distal end of the main body stent graft and the central support sealing ring.

11. The stent graft of claim 6, wherein the plurality of sealing rings includes a distal sealing ring coupled to the main body stent graft at or directly adjacent to the distal end of the main body stent graft.

12. The stent graft of claim 1, wherein two renal openings are defined in the sidewall of the main body stent graft distal to the diaphragm.

13. The stent graft of claim 12, wherein the distal sealing ring has two radial portions joined by two arch portions, wherein the two arch portions are arranged longitudinally along the sidewall of the main body stent graft and the two radial portions are arranged about the circumference of the main body stent graft, and wherein the two arch portions are aligned with the two renal openings.

14. The stent graft of claim 13, wherein an effective diameter extending between the two radial portions of the distal sealing ring ranges from about 20 mm to about 50 mm.

15. The stent graft of claim 1, wherein a pair of opposing helical stent structures are coupled to one or more of the first renal lumen, the second renal lumen and the infrarenal lumen.

16. The stent graft of claim 1, wherein the diaphragm has an expandable frame, wherein the expandable frame is configured to apply an outward radial force to the main body stent graft.

17. The stent graft of claim 1, wherein the proximal end of the main body stent graft is coupled to a fixation stent.

18. The stent graft of claim 1, wherein the infrarenal lumen has a diameter ranging from about 10 mm to about 25 mm.

19. The stent graft of claim 1, wherein the first and second renal inlets each have a diameter ranging from about 4 mm to about 25 mm.

20. The stent graft of claim 1, wherein the first and second renal lumens each have a diameter ranging from about 4 mm to about 12 mm.

21. The stent graft of claim 1, wherein the diameter of each of the first and second renal inlets is larger than the diameter of each of the first and second renal lumens, wherein a proximal end of each of the first and second renal lumens is tapered.

22. The stent graft of claim 1, wherein the visceral inlet is defined as a V-shape, a half-circle having a radius ranging from about 5 mm to about 15 mm or a complete circular opening with a diameter ranging from about 8 mm to about 12 mm.

23. The stent graft of claim 1, wherein the visceral-vessel opening is wider at a proximal end than at a distal end.

24. A stent graft, comprising:
a main body stent graft defining a lumen having an inlet defined at a proximal end of the main body stent graft and having an outlet defined at a distal end of the main body stent graft;
a diaphragm disposed within the lumen of the main body stent graft and coupled to the main body stent graft, wherein a first renal inlet, a second renal inlet, an infrarenal inlet and a visceral inlet are defined in the diaphragm;
a first renal stent graft coupled to the first renal inlet, wherein the first renal stent graft defines a lumen;
a second renal stent graft coupled to the second renal inlet, wherein the second renal stent graft defines a lumen; and
an infrarenal stent graft coupled to the infrarenal inlet, wherein the infrarenal stent graft defines a lumen, and wherein the infrarenal lumen has a length of at least 30 mm.

25. The stent graft of claim 24, wherein the diameter of the infrarenal inlet is larger than the diameter of the infrarenal lumen, wherein a proximal end of the infrarenal lumen is tapered.

26. A stent graft, comprising:
a main body stent graft defining a lumen having an inlet defined at a proximal end of the main body stent graft and having an outlet defined at a distal end of the main body stent graft;
a diaphragm disposed within the lumen of the main body stent graft and coupled to the main body stent graft, wherein a first renal inlet, a second renal inlet, an infrarenal inlet and a visceral inlet are defined in the diaphragm;
a first renal stent graft coupled to the first renal inlet, wherein the first renal stent graft defines a lumen;
a second renal stent graft coupled to the second renal inlet, wherein the second renal stent graft defines a lumen; and
an infrarenal stent graft coupled to the infrarenal inlet, wherein the infrarenal stent graft defines a lumen, and wherein the infrarenal inlet has a diameter ranging from about 10 mm to about 25 mm and wherein the diameter of each of the first and second renal inlets is larger than the diameter of each of the first and second renal lumens, wherein a proximal end of each of the first and second renal lumens is tapered.

27. A method for placement of a stent graft, the method comprising:
introducing a guidewire into any appropriately sized arterial configuration via arterial access;
loading a delivery catheter containing the stent graft of claim 1 onto the guidewire;
moving the delivery catheter along the guidewire and introducing the delivery catheter into the appropriately sized arterial configuration via arterial access; and
deploying the stent graft into the appropriately sized arterial configuration and/or a lumen of a previously-placed stent graft.

28. The method of claim 27, further comprising:
loading a second delivery catheter containing a bridging stent graft onto the guidewire;
moving the second delivery catheter along the guidewire and introducing the second delivery catheter into the proximal end of main body lumen of the stent graft via arterial access;
selecting from among a first renal inlet, a second renal inlet, an infrarenal inlet or a visceral inlet defined in a diaphragm;
introducing the second delivery catheter into the selected inlet and into either a lumen coupled to the selected inlet or an appropriately sized arterial lumen; and
deploying all or a portion of the bridging stent graft into the selected inlet or the appropriately sized arterial lumen.

* * * * *